United States Patent [19]

Orlando et al.

[11] 3,956,403

[45] May 11, 1976

[54] BROMINATED BIPHENOLS

[75] Inventors: Charles M. Orlando; Francois A. Lavallee, both of Schenectady, N.Y.

[73] Assignee: General Electric Company, Schenectady, N.Y.

[22] Filed: Aug. 18, 1975

[21] Appl. No.: 605,399

Related U.S. Application Data

[62] Division of Ser. No. 169,517, Aug. 5, 1971.

[52] U.S. Cl. .......................... 260/620; 260/396 R; 260/619 R
[51] Int. Cl.² .................. C07C 37/00; C07C 37/12
[58] Field of Search ............ 260/620, 619 D, 396 R

[56] References Cited
UNITED STATES PATENTS

| | | | |
|---|---|---|---|
| 3,306,875 | 2/1967 | Hay | 260/396 R |
| 3,491,128 | 1/1970 | Dewhurst | 260/396 R |
| 3,720,721 | 3/1973 | Becker et al. | 260/620 |
| 3,894,094 | 7/1975 | Rultedge | 260/620 |

OTHER PUBLICATIONS
Auwer, "Ber.", 38, 226, (1905).

*Primary Examiner*—Norman Morgenstern
*Attorney, Agent, or Firm*—F. Wesley Turner; Joseph T. Cohen; Jerome C. Squillaro

[57] ABSTRACT

Bromobiphenols containing at least two bromine atoms meta to the phenolic hydroxyl groups can be produced from 3,3',5,5'-tetra-substituted diphenoquinones by reacting the latter with bromine. The reaction can be controlled to produce little, if any, byproduct. The products obtained are dependent to some extent on the substituents in the four positions ortho to the hydroxyl groups. The biphenols can be used as antioxidants or as starting materials for preparation of flame-retardent polymeric compositions useful in the molding, coating and insulating arts.

6 Claims, No Drawings

BROMINATED BIPHENOLS

This is a division of application Ser. No. 169,517, filed Aug. 5, 1971.

This invention relates to bromobiphenols. More particularly, the invention relates to 2,2',6,6'-tetrasubstituted p,p'-biphenols having the formula,

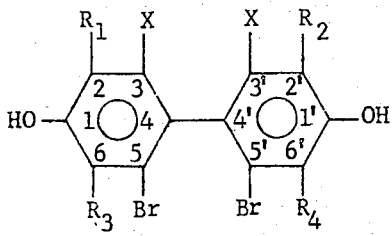

where $R_1$, $R_2$, $R_3$ and $R_4$ are primary lower alkyl, phenyl or 4-bromophenyl and each X is hydrogen when $R_1$, $R_2$, $R_3$ or $R_4$ is other than primary lower alkyl and each X is independently hydrogen or bromine when $R_1$, $R_2$, $R_3$ and $R_4$ are primary lower alkyl. These compounds are readily made by reacting bromine with diphenoquinones having the formula,

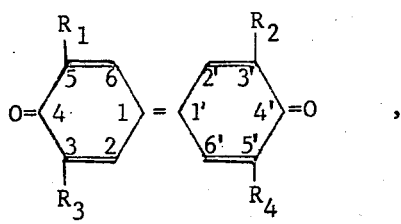

where $R_1$, $R_2$, $R_3$ and $R_4$ are as defined above with respect to the biphenols. The numbers in the rings in the above formulae are to aid the reader in locating the ring positions of the substituents of the compounds recited hereinafter which are named according to accepted rules of nomenclature.

In the copending application, Ser. No. 53,648, filed July 9, 1970, and assigned to the same assignee as the present invention, Hans-Dieter Becker discloses the preparation of monochlorobiphenols by reaction of hydrogen chloride with diphenoquinones. In order to produce higher chlorinated biphenols, the initial monochlorobiphenol must be reoxidized to the chlorodiphenoquinone and then further reacted with additional hydrogen chloride. Becker reviews the prior art method of preparing chlorinated biphenols pointing out that mixtures of polychlorinated products were obtained rather than a single product which could be easily purified from minor impurities. No corresponding work has apparently been done on the preparation of brominated biphenols. In view of the desirability of preparing flame-proof plastics, it would be highly desirable to prepare starting materials such as biphenols having a high halogen content wherein the halogen is stable under the conditions used in preparing the polymers and in fabricating the resulting polymers into fabricated articles and yet would still impart flame resistance to the polymers.

In our attempts to prepare biphenols containing more than one halogen, we have confirmed the results of prior workers that use of chlorine to produce biphenols containing more than one chlorine in a single step reaction leads to a mixture of polychlorinated products which are difficult to separate and purify. Surprisingly, we have found that bromine can be used to produce polybrominated biphenols in a reaction where a single, desired product can be produced in a high yield. This is accomplished by reacting a 3,3',5,5'-tetrasubstituted diphenoquinones with bromine.

If the reaction is run by adding the diphenoquinone to liquid bromine, a single polybrominated product is obtained which is dependent on the four substituents on the starting diphenoquinone. When these substituents are all primary alkyl groups, the four unsubstituted diphenoquinone ring positions are brominated yielding 2,2',6,6'-tetraalkyl-3,3',5,5'-tetrabromo-p-p'-biphenol. If the alkyl groups are secondary alkyl groups, dealkylation of some of the secondary alkyl groups occurs with bromination of the positions so vacated occurring. If tertiary alkyl groups are present, complete dealkylation occurred and some of the vacated positions are brominated. Since this dealkylation reaction introduces bromine into the position ortho to the hydroxyl groups, it is undesirable since the bromine groups in these positions are less stable in subsequent use to form polymers and especially during molding. For this reason, we prefer that the alkyl groups be primary alkyl groups and still, more preferably, primary lower alkyl groups.

When the four substituents of the diphenoquinone are phenyl, only two of the unsubstituted diphenoquinone ring positions are brominated and the para position of all four of the phenyl groups are brominated so that the product is the hexabromo compound, 3,3'-dibromo-2,2',6,6'-tetra(4-bromophenyl)-p,p'-biphenol. When the four substituents on the diphenoquinone are both primary alkyl and phenyl, only two of the unsubstituted diphenoquinone ring positions are brominated and the para position of the two phenyl groups are brominated. The two diphenoquinone ring positions which are brominated are those adjacent to the ring position occupied by the phenyl groups. For example, when the diphenoquinone is 3,3'-dimethyl-5,5'-diphenyldiphenoquinone, the product is the tetrabromobiphenol, 3,3'dibromo-2,2'-bis(4'-bromophenyl)-6,6'-dimethyl-p,p'-biphenol.

It will be recognized that in using liquid bromine as the reaction medium sufficient bromine must be used to maintain a liquid phase for the reaction. This means that more than the stoichiometric amount of bromine is present than is required for the formation of the above products. In view of this excess bromine, it was indeed surprising to find that only a single product from any one diphenoquinone is obtained rather than a mixture of products and that some higher brominated products were not formed, especially in the case of the phenyl substituted diphenoquinones.

From these results, it appears that the initial bromination reaction involves two of the unsubstituted ring positions of the diphenoquinone with the other two unsubstituted ring positions being unreactive towards further bromination unless all four substituents of the starting diphenoquinone are primary alkyl groups, in which case the other two unsubstituted ring positions can be brominated and the alkyl groups remain unbrominated. When there is a phenyl substituent present, bromination proceeds until two of the unsubstituted ring positions of the diphenoquinone are brominated and further bromination involves only the para position of the phenyl substituent and then stops. This indeed is surprising in view of the excess bromine present in the reaction.

Because of the high vapor pressure of bromine, and because gaseous hydrogen bromide is formed by the bromination reaction, loss of bromine from the reaction vessel can occur if precautions, for example, use of a highly efficient condenser, are not used. This problem is accentuated if temperatures higher than ambient room temperature are used. Furthermore, the reaction of the diphenoquinone with bromine is an exothermic reaction. In order to maintain a liquid phase at all times, the diphenoquinone is preferably added to the liquid bromine, generally with cooling of the reaction vessel, and the rate of addition of the diphenoquinone controlled so as to not obtain an uncontrollable exotherm. The problem with volatility of the bromine and the exotherm can be alleviated by use of a nonreactive solvent, for example perhalogenated hydrocarbons, preferably aliphatic having a relatively low boiling point so that they may be evaporated from the reaction mixture. A typical example is carbon tetrachloride, but other known solvents for halogenation reactions are well-known in the art and can be used.

When a solvent is used for the bromination reaction, the reaction does not proceed as readily to give the single brominated products mentioned above and mixtures with lower brominated products are obtained. In order to obtain the same products as are obtained with use of liquid bromine, heating of the reaction mixture after any exotherm has occurred will cause further bromination but the use of a Friedel-Crafts catalyst, for example, tin or zinc halides, preferably the bromides, are very effective in increasing the extent of the bromination of reactions run in solution so that the results are comparable to those obtained when liquid bromine is used. The use of the solvent can be of advantage when lower brominated products than those mentioned above are desired, for example, the dibrominated product where only the unsubstituted ring position of the diphenoquinone is brominated or, in addition, when phenyl substituents are present, some but not all of the phenyl substituents are brominated, for example, 3,3'-dibromo-2,2',6,6'-tetramethyl-p,p'-biphenol, 3,3'-dibromo-2,2'-bis(4-bromophenyl)-6,6'-diphenyl-p,p'-biphenol, etc. In this case, mixtures of brominated products will be obtained unless the usual precautions are taken, for example, use of less than a stoichiometric amount of bromine required for the desired brominated product, but this adversely affects the yield, addition of the bromine to the diphenoquinone dissolved in or suspended in a solvent in which it is at least partially soluble, etc.

We have found that for introduction of only two bromine groups, that the stoichiometric amount is one mole of bromine for each mole of diphenoquinone. Apparently, the first step in the bromination reaction is the addition of one molecule of bromine with the production of one molecule of HBr which then in turn reacts with the intermediate product producing the dibromo product. Subsequent bromination reactions are of the usual type where for each additional mole of bromine, one atom of bromine is introduced into the product molecule and one molecule of hydrogen bromide is evolved. We have obtained good yields of the dibrominated product when using 1.5 moles of bromine per mole of diphenoquinone.

One of the convenient ways of making the 3,3',5,5'-tetra-substituted diphenoquinones starting materials is disclosed in U.S. Pat. No. 3,306,875-Allan S. Hay, issued Feb. 28, 1967 and assigned to the same assignee as the present invention. This reaction involves oxidative coupling of a 2,6-disubstituted phenol using a basic cupric salt-amine complex. In this reaction, the two moieties of the diphenoquinone would bear the same two substituents since two molecules of the same phenol are coupled together to form the diphenoquinone.

Although it would be possible to prepare diphenoquinones from a mixture of two phenols, the reaction would not be straightforward and would produce a mixture of all three possible products. Because of this, the most readily available tetra-substituted diphenoquinones are those in which all four substituents are identical or in which the two substituents on one ring are different but identical with the two different substituents on the other ring, i.e. the diphenoquinones would have the formula given previously where the $R_1$, $R_2$, $R_3$ and $R_4$ substituents are all identical or $R_1$ and $R_3$ are different and $R_2$ and $R_4$ are the same as $R_1$ and $R_3$. It is to be recognized that two different isomeric diphenoquinones are possible, one being where $R_1$ is the same as $R_4$ but different from $R_2$ which is the same as $R_3$ and the other being where $R_1$ is the same as $R_2$, but is different than $R_3$ which is the same as $R_4$. Such isomers are known but it is not material to the making of our products since it is to be recognized that the bromination reaction converts the two isomeric diphenoquinones into the same brominated biphenol products.

Although we prefer to use those diphenoquinones where all four substituents are identical or the two substituents on the one ring are different but the same as the two substituents on the other ring, because of the ease of preparation, the other 3,3',5,5'-tetra-substituted diphenoquinones can be used in our process.

Typical examples of the primary lower alkyl groups are methyl, ethyl, propyl, butyl, pentyl, hexyl, cyclohexyl, heptyl, octyl. Although other aryl substituents other than phenyl can be substituents on the diphenoquinone, such diphenoquinones are not readily available and therefore we prefer the aryl substituent be phenyl.

In order that those skilled in the art may better understand our invention, the following examples are given by way of illustration, and not by way of limitation. In all of the examples, parts are by weight and temperatures are given in degrees Centigrade unless otherwise stated. Where elemental analyses are given, the theoretical value for the compound is given in parentheses following the determined value.

The general procedure used with liquid bromine was to add the diphenoquinone slowly to a flask containing the liquid bromine at room temperature with stirring. Since an exothermic reaction occurs on the addition of the diphenoquinone, the amount and rate of addition was controlled so that the temperature did not exceed 40°–45° to minimize the loss of bromine in the hydrogen bromide which was evolved. When the amount of diphenoquinone was 1 to 5 g., the addition was usually completed within 15 minutes. After the diphenoquinone addition was completed, the reaction mixture was stirred at room temperature so that the total reaction time was two hours. The residual hydrogen bromide and the excess bromine were removed from the reaction mixture under a slow stream of nitrogen. The solid residue was then purified by recrystallization.

EXAMPLE 1

Using the general procedure, 3.7 g. of 3,3',5,5'-tetramethyldiphenoquinone was added to 4 ml. of bromine. There was obtained 8.5 g., a quantitative yield of 3,3',5,5'-tetrabromo-2,2',6,6'-tetramethyl-p,p'-biphenol having a melting point of 244°–246°. Elemental analysis showed: C, 34.44 (34.4); H, 2.52 (2.5); Br, 57.3 (57.2). The nmr spectrum showed that the methyl groups were not brominated.

When this example was repeated on a larger scale scale using 37 g. of 3,3',5,5'-tetramethyldiphenoquinone and adding it over ½ hour to 120 g. of liquid bromine at room temperature, a tan colored solid was obtained on evaporation of the excess bromine after 2 hours which after suspending in 200 ml. of acetone, filtered and dried gave an 86 g. yield of the above product; nmr ($\delta$ pp,., CCl$_4$-acetone-d$_6$): 2.38 (S, 6, ArCH$_3$), 7.7 (S, 1, OH); mass spec. m/e: M$^+$ 554–562 (quintet). $\lambda_{max}^{95\% \, Etoh}$ nm ($\epsilon$): 283 (2290), 296 (2500).

When 1 g. of 3,3',5,5'-tetramethyldiphenoquinone was added to 6 ml. of liquid chlorine at −70° and the reaction mixture placed in an ice water bath permitting the chlorine to vaporize for a 2 hour period, a white amorphous solid remained which could not be further purified. A sample of the chlorinated product was then reduced with zinc dust and acetic acid to give a mixture of biphenols. The major products were the nonchlorinated 2,2',6,6'-tetramethyl-p,p'-biphenol, the monochlorinated product 3-chloro2,2',6,6'-tetramethyl-p,p'-biphenol and the dichloro compound 3,3'-dichloro-2,2',6,6'-tetramethyl-p,p'-biphenol.

EXAMPLE 2

Using the general procedure, 0.5 g. of 3,3',5,5'-tetraethyldiphenoquinone was reacted with 2 ml. of bromine to give 0.186 grams, a 20% yield of 3,3',5,5'-tetrabromo-2,2'-6,6'-tetraethyl-p,p'-biphenol having a melting point at 202°–204°. Elemental analysis showed: C, 38.7 (39.1); H, 3.6 (3.61), Br, 52.1 (52.05). Its nmr spectrum showed no aromatic protons and that the ethyl groups had not been brominated; nmr ($\delta$ ppm., CDCl$_3$): 1.15 (triplet, 6, CH$_2$CH$_3$), 2.9 (quartet, 4, CH$_2$CH$_3$), 4.98 (S, 1, OH); mass spec. m/e: M$^+$ 610–618 (quintet). $\lambda_{max}^{95\% \, Etoh}$ nm ($\epsilon$): 283 (3040), 292 (3422).

EXAMPLE 3

Using the general procedure, 4.8 g. of 3,3',5,5'-tetraphenyldiphenoquinone was added to 5 ml. of bromine. There was obtained a yield of 1.01 g. (13%) of 3,3'-dibromo-2,2',6,6'-tetra(4-bromophenyl)-p,p'-biphenol having a melting point of 265°–267°. It was identified by its nmr and mass spectra; nmr ($\delta$ ppm., C$_6$D$_6$): 4.64 and 4.82 (S, 1, OH), 7.1–7.24 (m, 9, ArH); mass spec. m/e: M$^+$ 958–970 (septet).

When 3,3',5,5'-tetraisopropyldiphenoquinone was brominated according to the general procedure, the main product isolated in a 25% yield had a melting point of 175°–177°. It was a partially dealkylated product containing 2 isopropyl groups and 4 bromine substituents, 2 of them in ortho positions with respect to the hydroxyl group and 2 of them in meta positions with respect to the hydroxyl groups. When 3,3',5,5'-tetra-t-butyldiphenoquinone was brominated according to the general procedure, a completely dealkylated product, melting point 216°–218° containing no t-butyl groups was obtained in a 98% yield. It had 5 bromine groups, 3 of them in the ortho positions with respect to the hydroxyl groups and 2 of them in the metal position with respect to the hydroxyl groups. When 3,3'-di-t-butyl-5,5'-dimethyldiphenoquinone was brominated according to the general procedure, the main product obtained in a 13% yield had a melting point of 193°–195°. It was completely devoid of t-butyl substituents still contained the two methyl groups and contained 4 bromine substituents, 2 in the ortho positions and 2 in the meta positions with respect to the phenolic hydroxyl groups. The meta positions, with respect to the hydroxyl groups, which were adjacent to the methyl groups, were not brominated.

EXAMPLE 4

A suspension of 1.0 g. of 3,3'-dimethyl-5,5'-diphenyldiphenoquinone in a solution of 0.65 g. of bromine in 5 ml. of carbon tetrachloride was stirred at room temperature for 40 hours. The reaction mixture was filtered and the precipitate recrystallized from a mixture of hexane and benzene to give 0.518 g. (37% yield) of 3,3'-dibromo-2,2'-diphenyl 6,6'-dimethyl-p,p'-biphenol having a melting point of 244°–247°. Its elemental analysis showed: C, 59.1 (59.54), H, 3.9 (3.81); mass spec. m/e M$^+$ 522–526 (triplet); nmr ($\delta$ ppm, CDCl$_3$): 2.46 (doublet-J=0.6 Hz, 3, ArCH$_3$), 5.40 (S, 1, —OH), 6.96 (quartet-J=0.6 Hz, 1, ArH), 7.4 (S, 5, ArH).

EXAMPLE 5

Using the general procedure, 2 g. of 3,3'-dimethyl-5,5'-diphenyldiphenoquinone was reacted with 5 ml. of bromine. The product was a dark oil which was triturated with a mixture of acetone and benzene to give a solid product which after recrystallization from a hexane-dioxane mixture gave 0.377 g. of white crystals of 3,3'-dibromo-2,2'-bis-(4-bromophenyl)-6,6'-dimethyl-p,p'-biphenol having a melting point of 324°. Analysis: C, 45.9 (45.61); H, 2.8 (2.92); mass spec.; m/e M$^+$ 678–686 (quintet); nmr ($\delta$ ppm, d-DMF): 2.48(doublet-J=0.5Hz, 3,ArCH$_3$), 7.02 (quartet-J=0.5Hz, 1, ArH), 7.52 (A$_2$B$_2$ pattern, 4, ArH), 7.96 (S, 1, OH).

EXAMPLE 6

This example shows the effect of solvent. To a solution of 16.5 g. of bromine dissolved in 10 ml. of carbon tetrachloride, 5 g. of 3,3',5,5'-tetramethyldiphenoquinone was added. After heating the reaction mixture at 70° for 6 hours and 35 minutes, analysis by vapor phase chromatography showed that the mixture was approximately 75%, 3,3',5,5'-tetrabromo-2,2',6,6'-tetramethyl-p,p'-biphenol and 25%, 3,3', 5-tribromo-2,2',6,6'-tetramethyl-p,p'-biphenol.

EXAMPLE 7

This example illustrates the further bromination of the mixture of lower brominated products. When 50.6 g. of bromine was added to a suspension of of 18.5 g. of 3,3',5,5'-tetramethyldiphenoquinone at room temperature and the reaction allowed to proceed for 2 hours, there was obtained a yield of 30.1 g. of a product having a melting point of 227°–237°. Gas chromatographic analysis of the product showed that it was approximately 13% 3,3'-dibromo-2,2',6,6'-tetramethyl-p,p'-biphenol, 76% 3,3',5-tribromo-2,2',6,6'-tetramethyl-p,p'-diphenol and 11% 3,3',5,5'-tetrabromo-2,2',6,6'-tetramethyl-p,p'-biphenol. A two gram sample of this mixture was added to 5 ml. of bromine at room temperature. After two hours gas chromotography showed that the product was now all the tetrabromo compound.

EXAMPLE 8

This example shows the benefit to be obtained by using a Friedel-Crafts catalyst when a solvent is used. To demonstrate the effect of the catalyst, the reaction was run both with and without the catalyst. The general procedure used was to place 5 g. of 3,3′,5,5′-tetramethyldiphenoquinone and 10 ml. of carbon tetrachloride in a 3-neck flask fitted with a thermometer, reflux condenser and dropping funnel. Liquid bromine was then added to the reaction mixture and the reaction mixture heated at 70° for 4.5 hours. At the end of this time, the reaction mixture was sampled and analyzed by gas chromatography. The catalyst was then added and the reaction continued at room temperature for an additional 1.5 hours. In one case, a 25 molar excess of bromine was used resulting in a product mix which was 77% 3,3′,5,5′-tetrabromo-2,2′,6,6′-tetramethyl-p,p′-biphenol and 23% 3,3′,5-tribromo-2,2′,6,6′-tetramethyl-p,p′-biphenol. After adding 0.5 g. of stannous chloride as a catalyst, the yield of the tetrabromobiphenol was increased to 88% and the yield of the tribromobiphenol decreased to 12%.

When a 65% molar excess of bromine was used, the yield of the tetrabromobiphenol was 73% without catalyst. After adding 0.5 g. of zinc bromide as catalyst, the yield of tetrabromobiphenol was increased to 86% and the yield of tribromobiphenol decreased to 14%. When repeated with the $ZnBr_2$ in the initial reaction mixture, after only 2 hours at 70° the yield of tetrabromo compound was 76% and the yield of tribromo compound was 24%. The results of this example show that the molar ratio of the bromine has little if any significant effect whereas the use of the Friedel-Crafts catalyst has a very significant and outstanding effect on the yield of the tetrabromo product.

The brominated biphenols of this invention can be used as anti-oxidants for petroleum products, such as gasoline, and as stabilizers against polymerization of monomeric materials to maintain them in the essentially unpolymerized state until such time as they are ready for polymerization, for instance, with an organic peroxide. In addition, the halobiphenols can be reacted with isophthaloyl or terephthaloyl halides to make polymers in accordance with the procedures described in U.S. Pat. Nos. 3,036,990–992, issued May 29, 1962, and U.S. Pat. Nos. 3,160,602–605, issued Dec. 12, 1964, in the names of S. W. Kantor and F. F. Holub, all assigned to the same assignee as the present invention. The aromatic polyesters thus obtained can be used for making films and fibers, and can also be employed for making solutions of such polymers and thereafter coated on electrical conductors to form high temperature insulation. The presence of halogen in the dihydric biphenyl reactant imparts improved flame-resistance to such polymers. Other polyesters can be made by reacting the halobiphenols with aliphatic dicarboxylic acids, or acyl halides thereof, such as adipic acid, sebacic acid, adipoyl chloride, etc.

Alternatively, polycarbonate resins suitable for molding and films can be obtained in accordance with the methods outlined in U.S. Pat. No. 3,022,272, issued Feb. 20, 1962, and U.S. Pat. No. 3,018,365, issued Apr. 3, 1962, by treatment of the halobiphenols with a phosgenating agent, e.g., diphenyl carbonate, $COCl_2$, chloroformate, etc.

In addition, the brominated biphenols can be converted to esters of monocarboxylic acids for use as plasticizers, reacted with ethylene oxide to form the bis(2-hydroxyethyl) ether which in turn can be incorporated into either polyesters or polycarbonates or made into plasticizers, reacted with epichlorohydrin to form the bisglycidyl ethers useful in making epoxy resins, etc. For example, the following derivatives have been prepared by reaction of 3,3′,5,5′-tetrabromo-2,2′,6,6′-tetramethyl-p,p′-biphenol with the following reagents: (1) Ethylene chlorohydrin was reacted in the presence of a water-ethanol solution of sodium hydroxide to prepare the mono(2-hydroxyethyl) ether and the bis(2-hydroxyethyl) ether, depending on the molar ratio of the two reactants. The bis(2-hydroxyethyl) ether was further reacted with additional ethylene chlorohydrin to convert one of the 2-hydroxyethyl ether groups to a 2-(2-hydroxyethoxy) ethyl ether group. (2) After reacting the biphenol with sodium methylate to prepare the di-sodium salt, the latter was reacted as the dry salt with α-epichlorohydrin to prepare the diglycidyl ether. (3) A mixture of acetic acid and acetic anhydride to prepare the diacetate ester. (4) Allyl chloride to prepare the diallyl ether. (5) Cyanogen bromide to replace both hydroxy groups with —CN groups. The products of reactions 1, 2, 4 and 5, like the bromobiphenols of this invention have been converted to various polymers.

For example, the products of reactions 4 and 5 are polymerizable when heated with or without a polymerization catalyst. They can be polymerized alone or with other polymerizable monomers. The products of reaction 3 are converted to epoxy resins, either alone or with other epoxides, by reaction with monomeric or polymeric diols in the presence of polyamine or anhydride catalysts. The products of reactional 1 can be reacted to form polyesters with dicarboxylic acids by ester interchange with low molecular weight glycols, e.g., 1,4-butanediol, etc., polyesters of terephthalic acid in the presence of a transesterification catalyst to produce homopolyesters as well as copolyesters. These polyesters, like the other polymers described above have flame-resistant properties per se, or can be blended with other polymers to impart flame-resistant properties to the blends. Other additives known to increase the flame-resistance of halogen containing polymers, for example, antimony oxide can also be added to further increase the flame-resistant properties Obviously, other modifications or variations of the present invention are possible in light of the above teachings and disclosures. It is, therefore, to be understood that changes may be made in the particular embodiments of the invention described which are within the full intended scope invention as defined by the appended claims.

What I claim as new and desire to secure by Letters Patent of the United States is:

1. A bromination process which comprises contacting liquid bromine with a diphenoquinone of the formula

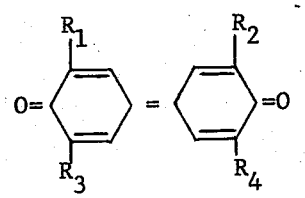

where independently each $R_1$, $R_2$, $R_3$ and $R_4$ is a normal methyl, ethyl, propyl, butyl, pentyl, hexyl, heptyl or octyl radical or is a cyclohexyl radical, and recovering a biphenol of the formula

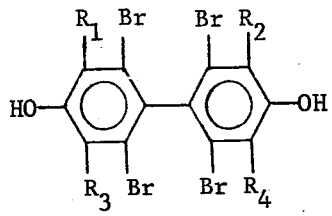

where each $R_1$, $R_2$, $R_3$ and $R_4$ is as previously defined.

2. The process of claim 1, wherein the mole ratio of bromine to diphenoquinone is at least greater than about 1.5:1.

3. The process of claim 2, wherein the diphenoquinone is added to the liquid bromine at about ambient room temperature.

4. The process of claim 3, wherein the resulting reaction mixture is heated at elevated temperatures to complete the bromination reaction.

5. The process of claim 1, wherein independently each $R_1$, $R_2$, $R_3$ and $R_4$ is a methyl radical.

6. The process of claim 4, wherein each $R_1$, $R_2$, $R_3$ and $R_4$ is a methyl radical.

* * * * *